US012715837B2

(12) United States Patent
Ehlis et al.

(10) Patent No.: US 12,715,837 B2
(45) Date of Patent: Aug. 25, 2026

(54) PROCESS FOR ISOLATING 2-(4'-DIETHYLAMINO-2'-HYDROXYBENZOYL)BENZOIC ACID HEXYL ESTER

(71) Applicant: BASF SE, Ludwigshafen am Rhein (DE)

(72) Inventors: Thomas Ehlis, Schweizerhalle (CH); Karin Schein-Albrecht, Ludwigshafen am Rhein (DE); Mathieu Blanchot, Ludwigshafen am Rhein (DE); Dennis Kaufhold, Ludwigshafen am Rhein (DE); Sebastian Wloch, Ludwigshafen am Rhein (DE); Helmut Kronemayer, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 840 days.

(21) Appl. No.: 17/802,171

(22) PCT Filed: Feb. 25, 2021

(86) PCT No.: PCT/EP2021/054638

§ 371 (c)(1),
(2) Date: Aug. 25, 2022

(87) PCT Pub. No.: WO2021/170695

PCT Pub. Date: Sep. 2, 2021

(65) Prior Publication Data

US 2023/0357129 A1 Nov. 9, 2023

(30) Foreign Application Priority Data

Feb. 27, 2020 (EP) .................................... 20159898
May 15, 2020 (EP) .................................... 20174956

(51) Int. Cl.
*C07C 227/42* (2006.01)
*C07C 229/52* (2006.01)

(52) U.S. Cl.
CPC .......... *C07C 227/42* (2013.01); *C07C 229/52* (2013.01); *C07B 2200/13* (2013.01)

(58) Field of Classification Search
None
See application file for complete search history.

(56) References Cited

U.S. PATENT DOCUMENTS

2005/0165099 A1 7/2005 Heidenfelder et al.
2014/0349115 A1 11/2014 Champ et al.

FOREIGN PATENT DOCUMENTS

| | | | |
|---|---|---|---|
| CN | 101675029 A | | 3/2010 |
| DE | 10011317 A1 | | 9/2001 |
| EP | 2155660 A1 | | 2/2010 |
| IN | 202227037724 | * | 2/2023 |
| JP | 09-278683 A | | 10/1997 |
| JP | 09-278983 A | | 10/1997 |
| JP | 2005-533764 A | | 11/2005 |
| JP | 2010-525009 A | | 7/2010 |
| KR | 10-2020-0002720 A | | 1/2020 |
| WO | 03/97578 A1 | | 11/2003 |
| WO | 2008/135360 A1 | | 11/2008 |

OTHER PUBLICATIONS

"Process for Isolating 2-(4'-Diethylamino-2'-Hydroxybenzoyl)Benzoic Acid Hexyl Ester", vol. 4, No. 1, Feb. 2017, pp. 1-11.

Ashizawa, "Evaluating the Physical Properties of the Molecular Details of Pharmaceutical Crystals (12) Salt and Crystal Form Optimization and Crystallization Technology", Department of Physical Chemistry, Tsukuba Research Laboratories, Research and Development, vol. 18, No. 10, Feb. 2025, pp. 1-45.

European Search Report for EP Patent Application No. 20159898.4, Issued on Sep. 1, 2020, 7 pages.

International Search Report and Written Opinion received for PCT Patent Application No. PCT/EP2021/054638, mailed on May 3, 2021.

Reed, "Optimization and Crystallization Technology of Salt and Crystal Form", Pharm Tech Japan, vol. 18, No. 10, 2002, pp. 81-96.

Tawa, "Chemistry Manual Volume on Applied Chemistry", vol. 7, No. 1, Jan. 30, 2014, pp. 269-270.

Grbovic et al., Synthesis, characterisation and aquatic ecotoxicity of the UV filter hexyl 2-(4-diethylamino-2- hydroxybenzoyl) benzoate (DHHB) and its chlorinated by-products, Environmental chemistry, vol. 13, No. 1, 2015, pp. 119-126.

Wang et al., Analysis on the Common Unqualified Items of Three Kinds of Special-Purpose Cosmetics-Based on the Results of the National Cosmetics Supervision and Sampling Inspection in 2018-2019, Chinese Journal of Medicinal Guide, 2020, 1 page.

Xiao et al., The preliminary evaluation of 17 kinds of sunscreens based on BASF sunscreen simulator, Modern Chemical Research, 2017, Retrieved from the internet at https://cnki.sris.com.tw/koms/detail/detailall.aspx? filename=ZJTY201705067&dbcode=CJFQ&dbname=CAPJ, pp. 1-4.

Masakuni Matsuoka, "Advancement of Organic Substance Crystallization Technology—Control of Particle Size, Form, Polymorph, and Purification", Pharm Tech Japan, vol. 19, No. 6, 2003, pp. 1-14.

Noriaki Hirayama, "Handbook for Producing Crystals of Organic Compounds", Maruzen Co., Ltd, 2008, pp. 1-29.

* cited by examiner

*Primary Examiner* — Renee Claytor
*Assistant Examiner* — Jennifer C Sawyer
(74) *Attorney, Agent, or Firm* — Faegre Drinker Biddle & Reath LLP

(57) ABSTRACT

The present invention relates to a process for isolating 2-(4'-diethylamino-2'-hydroxybenzoyl)benzoic acid hexyl ester with a high purity and low phthalic acid dialkyl ester content.

15 Claims, No Drawings

PROCESS FOR ISOLATING 2-(4'-DIETHYLAMINO-2'-HYDROXYBENZOYL) BENZOIC ACID HEXYL ESTER

CROSS-REFERENCE TO RELATED APPLICATIONS

This application is a national stage application (under 35 U.S.C. § 371) of PCT/EP2021/054638, filed Feb. 25, 2021, which claims benefit of European Application Nos. 20159898.4, filed Feb. 27, 2020, and 20174956.1, filed May 15, 2020, all of which are incorporated herein by reference in their entirety.

The present invention relates to a process for isolating 2-(4'-diethylamino-2'-hydroxybenzoyl)benzoic acid hexyl ester with a high purity and low phthalic acid dialkyl ester content.

UV radiation causes harmful effects on the human skin. Beside the acute effect of sunburn of the skin, UV radiation is also known to increase the risk of skin cancer. Furthermore, long time exposure to UV-A and UV-B light can cause phototoxic and photo allergenic reactions on the skin and can accelerate skin aging.

To protect the human skin from UV radiation, various sun protecting UV filters (also referred to as UV absorbers) exist including UV-A filter, UV-B filter, and broadband filters. These filters are added to sunscreen or cosmetic compositions. The UV filters are either organic or inorganic, particulate or non-particulate compounds, of which all have a high absorption efficacy in the UV-light range. In general, UV light can be divided into UV-A radiation (320-400 nm) and UV-B radiation (280-320 nm). Depending on the position of the absorption maxima, UV filters are divided into UV-A and UV-B filters. In case an UV filter absorbs both, UV-A and UV-B light, it is referred to as a broadband absorber.

Since 2006, the EU commission has recommended that all sunscreen or cosmetic compositions should have an UV-A protection factor, which is at least one third of the labelled sun protection factor (SPF), wherein the sun protection factor refers mainly to the UV-B protection.

2-(4'-Diethylamino-2'-hydroxybenzoyl)benzoic acid hexyl ester is an effective UV-A filter and is used to protect skin from UV radiation (e.g. in sunscreen). 2-(4'-Diethylamino-2'-hydroxybenzoyl)benzoic acid hexyl ester is depicted below, and will in the following also be referred to as compound of formula (I).

(I)

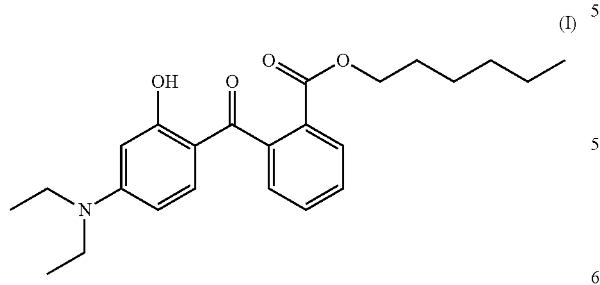

Processes of manufacturing 2-(4'-diethylamino-2'-hydroxybenzoyl)benzoic acid hexyl ester are known from e.g. DE 10011317, EP2155660, and WO 2003097578. In this connection, several challenges have been observed.

During synthesis, the by-product phthalic acid dihexyl ester (also known as PSDHE, dihexylphthalate) is formed.

The final product can still contain up to 50-150 ppm PSDHE. According to recent findings, the PSDHE content should be as low as possible, since this substance may according to the harmonised classification and labelling (ATP05) damage fertility and may damage the unborn child.

Further, during the synthesis of 2-(4'-diethylamino-2'-hydroxybenzoyl)benzoic acid hexyl ester process Rhodamine B type dyes (e.g. [9-(2-carboxyphenyl)-6-diethylamino-3-xanthenylidene]-diethylammonium salts) and corresponding esters are formed as impurities, which lead to an undesired discoloration of the final product. In order to purify the final product (less than 10 ppm Rhodamine B type dyes) an additional purification step is required. So far, the purification step comprises dissolution of the contaminated 2-(4'-diethylamino-2'-hydroxybenzoyl)benzoic acid hexyl ester in a nonpolar solvent such as cyclohexane or toluene, adsorption over an activated carbon or silicic acid bed and evaporation of the solvent after passage through the bed.

After the subsequent isolation of the 2-(4'-diethylamino-2'-hydroxybenzoyl)benzoic acid hexyl ester by separating off the toluene and/or 1-hexanol by distillation the clean end product is bottled as melt. Since the product is bottled as melt and first crystal growth occurs after storage for about six weeks at room temperature, the user has to heat the entire pack to a temperature above the melting point of 2-(4'-diethylamino-2'-hydroxybenzoyl)benzoic acid hexyl ester to be able to remove liquid product from the pack. In order to provide a form of crystalline end product, which is safe and easy to handle, the additional processing steps are required: a) providing a clear melt of 2-(4'-diethylamino-2'-hydroxybenzoyl)benzoic acid hexyl ester at a temperature above 57° C., b) crystallizing 2-(4'-diethylamino-2'-hydroxybenzoyl) benzoic acid hexyl ester at a temperature below 57° C., and c) comminuting the crystalline 2-(4'-diethylamino-2'-hydroxybenzoyl)benzoic acid hexyl ester to the desired particle size.

Hence, there is an ongoing need for a fast and efficient purification process of 2-(4'-diethylamino-2'-hydroxybenzoyl)benzoic acid hexyl ester. In this connection, it has been an object of the present invention to provide an optimized process for isolating crystalline 2-(4'-diethylamino-2'-hydroxybenzoyl)benzoic acid hexyl ester. It has especially been an object to provide a process for isolating crystalline 2-(4'-diethylamino-2'-hydroxybenzoyl)benzoic acid hexyl ester, wherein the amount of phthalic acid dihexyl ester is reduced. Further, it has been an object of the present invention to provide a process for isolating crystalline 2-(4'-diethylamino-2'-hydroxybenzoyl)benzoic acid hexyl ester, wherein the amount of colored impurities is reduced. Finally, it has been an object of the present invention to provide a fast process for isolating crystalline 2-(4'-diethylamino-2'-hydroxybenzoyl)benzoic acid hexyl ester, which further provides a safe and convenient to handle final product.

It has surprisingly been found that at least one of the above objects can be achieved by the process according to the present invention. The inventive process provides 2-(4'-diethylamino-2'-hydroxybenzoyl)benzoic acid hexyl ester with low PSDHE content (less than 15 ppm) and low content of colored impurities as free flowing crystals.

In particular, the inventors of the present invention have found a process for effectively purifying the compound of formula (I).

The present invention therefore relates in a first aspect to a process for isolating crystalline 2-(4'-diethylamino-2'-hydroxybenzoyl)benzoic acid hexyl ester comprising the steps of a) dissolving a mixture comprising 2-(4'-diethylamino-2'-hydroxybenzoyl)benzoic acid hexyl ester in a solvent having a boiling point of at most 110° C. to obtain a solution;

b) cooling the solution to a temperature in the range of from 20 to 40° C.;

c) optionally adding seed crystals of 2-(4'-diethylamino-2'-hydroxybenzoyl)benzoic acid hexyl ester to the solution;

d) cooling the solution to a temperature below 5° C. to obtain a suspension;

e) filtering the suspension to isolate 2-(4'-diethylamino-2'-hydroxybenzoyl)benzoic acid hexyl ester in crystalline form.

In the following, preferred embodiments of the process of the first aspect are described in further detail. It is to be understood that each preferred embodiment is relevant on its own as well as in combination with other preferred embodiments.

In a preferred embodiment A1 of the first aspect, the mixture in step a) comprises at least 85% by weight 2-(4'-diethylamino-2'-hydroxybenzoyl)benzoic acid hexyl ester and up to 15% impurities including solvent residues of solvents having a boiling point of more than 110° C. and phthalic acid dialkyl esters, wherein the weight-% amounts are in each case based on the total weight of the mixture.

In a preferred embodiment A2 of the first aspect, the impurities include 1-hexanol in an amount of up to 14% by weight based on the total weight of the mixture and phthalic acid dialkyl esters in an amount of from 50 to 200 ppm.

In a preferred embodiment A3 of the first aspect, the solvent in step a) has a boiling point of at most 85° C.

In a preferred embodiment A4 of the first aspect, the solvent in step a) is polar and/or is selected from methanol, ethanol, 1-propanol, and isopropanol.

In a preferred embodiment A5 of the first aspect, in step a) the mixture is dissolved at a temperature of from 45 to 55° C.

In a preferred embodiment A6 of the first aspect, wherein in step b) the solution is cooled to a temperature of from 25 to 30° C. over a period of at least 10 minutes.

In a preferred embodiment A7 of the first aspect, in step d) the solution is cooled to a temperature below −5° C. over a period of at least 3 hours, preferably at least 5 hours.

In a preferred embodiment A8 of the first aspect, cooling is performed via a linear or non-linear cooling rate.

In a preferred embodiment A9 of the first aspect, step d) further comprises stirring the obtained suspension at a temperature below 0° C. for at least 3 hours, preferably at least 6 hours.

In a preferred embodiment A10 of the first aspect, the process further comprises the step of f) washing the isolated 2-(4'-diethylamino-2'-hydroxybenzoyl)benzoic acid hexyl ester with a solvent, optionally an aqueous base, optionally a surfactant, and optionally water.

In a preferred embodiment A11 of the first aspect, the solvent in the washing step f) is the solvent as used in step a) of the process.

In a preferred embodiment A12 of the first aspect, the aqueous base in the washing step f) is present and is a potassium or sodium carbonate solution, a potassium or sodium hydrogen carbonate solution, a potassium or sodium hydroxide solution, or an aqueous ammonia solution.

In a preferred embodiment A13 of the first aspect, the surfactant in the washing step f) is present and is selected from the group consisting of alkylbenzylsulfonate, sodium lauryl sulfate, ammonium laureth sulfate, disodium lauryl sulfosuccinate, cocoamphocarboxy-glycinate, decyl polyglucoside, cetearyl alcohol, stearyl alcohol, cocamidopropyl betaine, decyl glucoside, glyceryl cocoate, sodium cocoyl Isethionate, almond glycerides, sodium lauryl sulpho-acetate, sodium lauroyl sarcosinate, sodium methyl cocoyl taurate, sucrose cocoate, polysorbate 20, and polysorbate 80, preferably dodecylbenzene sulfonic acid sodium salt.

In a preferred embodiment A14 of the first aspect, the process further comprises the step of g) drying the isolated 2-(4'-diethylamino-2'-hydroxybenzoyl)benzoic acid hexyl ester.

In yet another preferred embodiment A15 of the first aspect, the isolated 2-(4'-diethylamino-2'-hydroxybenzoyl) benzoic acid hexyl ester has a purity of at least 99%, a phthalic acid dialkyl ester content of less than 15 ppm, a 1-hexnol content of less than 400 ppm, and a Gardner value of 8.3 or lower, and wherein preferably the isolated 2-(4'-diethylamino-2'-hydroxybenzoyl)benzoic acid hexyl ester has a purity of at least 99%, a phthalic acid dialkyl ester content of less than 1 ppm, a 1-hexanol content of less than 200 ppm, a Gardner value of 8.3 or lower, and a rhodamine content of less than 1 ppm.

In a second aspect, the present invention relates to 2-(4'-diethylamino-2'-hydroxybenzoyl)benzoic acid hexyl ester having a purity of at least 99%, a phthalic acid dialkyl ester content of less than 15 ppm, a 1-hexanol content of less than 400 ppm, and a Gardner value of 8.3 or lower, and wherein preferably the 2-(4'-diethylamino-2'-hydroxybenzoyl)benzoic acid hexyl ester has a purity of at least 99%, a phthalic acid dihexyl ester content of less than 5 ppm, a 1-hexanol content of less than 200 ppm, a Gardner value of 8.3 or lower, and a rhodamine content of less than 1 ppm.

DETAILED DESCRIPTION

Before describing in detail exemplary embodiments of the present invention, definitions important for understanding the present invention are given.

As used in this specification and in the appended claims, the singular forms of "a" and "an" also include the respective plurals unless the context clearly dictates otherwise. In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only. Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below. It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

The term "compound according to the invention" or "compound of formula (I)" refers to 2-(4'-diethylamino-2'-hydroxybenzoyl)benzoic acid hexyl ester.

The term "halogen" denotes in each case fluorine, bromine, chlorine, or iodine, in particular fluorine, chlorine, or bromine.

The term "alkyl" as used herein denotes in each case a straight-chain or branched alkyl group having usually from 1 to 20 carbon atoms, preferably from 2 to 18 carbon atoms, more preferably 4 to 12 carbon atoms. Examples of an alkyl group are methyl, ethyl, n-propyl, isopropyl, n-butyl, 2-butyl, iso-butyl, tert-butyl, n-pentyl, 1-methylbutyl, 2-methylbutyl, 3 methylbutyl, 2,2-dimethylpropyl, 1 ethylpropyl, 1,1-dimethylpropyl, 1,2-dimethylpropyl, n-hexyl, n-heptyl, n-octyl, n-nonyl, n-decyl, n-undecyl, and n-dodecyl. Iso-butyl and n-hexyl are preferred, in particular n-hexyl.

The term "(Cn-Cm-alkyl)" as used herein denotes in each case a linker moiety, wherein the thereto attached moieties are attached to the terminal carbons.

The term "body-care product" refers to any product suitable to apply to the human body, e.g. sunscreen compositions, bath and shower products, preparations containing fragrances and odoriferous substances, hair-care products, dentifrices, decorative preparations, and cosmetic formulations containing active ingredients. Preferred are sunscreen compositions.

The term "sunscreen composition" or "sunscreen" or "skin-care product" refers to any topical product, which reflects and/or absorbs certain parts of UV radiation. Thus, the term "sunscreen composition" is to be understood as not only including sunscreen compositions, but also any cosmetic compositions that provide UV protection. The term "topical product" refers to a product that is applied to the skin and can refer, e.g., to sprays, lotions, creams, oils, foams, powders, or gels. According to the present invention the sunscreen composition may comprise one or more active agents, e.g., organic UV filters, as well as other ingredients or additives, e.g., emulsifiers, emollients, viscosity regulators, stabilizers, preservatives, or fragrances.

The term "daily care composition" refers to any topical product, which reflects or absorbs certain parts of UV radiation and is used as an everyday care product for the human body, e.g., for face, body or hair. The daily care composition may comprise one or more active agents, e.g., organic or inorganic UV filters, as well as other ingredients or additives, e.g., emulsifiers, emollients, viscosity regulators, stabilizers, preservatives, or fragrances.

Suitable bath and shower additives are, e.g., shower gels, bath-salts, bubble baths and soaps.

Suitable preparations containing fragrances and odoriferous substances are in particular scents, perfumes, toilet waters and shaving lotions (aftershave preparations).

Suitable hair-care products are, e.g., shampoos for humans and animals, in particular dogs, hair conditioners, products for styling and treating hair, perming agents, hair sprays and lacquers, hair gels, hair fixatives and hair dyeing or bleaching agents.

Suitable dentifrices are, e.g., tooth creams, toothpastes, mouth-washes, mouth rinses, anti-plaque preparations and cleaning agents for dentures.

Suitable decorative preparations are, e.g., lipsticks, nail varnishes, eye shadows, mascaras, dry and moist make-up, rouge, powders, depilatory agents and suntan lotions.

Suitable cosmetic formulations containing active ingredients are, e.g., hormone preparations, vitamin preparations, vegetable extract preparations and antibacterial preparations.

The cited body-care products can be in the form of creams, ointments, pastes, foams, gels, lotions, powders, make-ups, sprays, sticks or aerosols. They preferably contain the compound of formula (I) in the aqueous phase. Thereby, the compound of formula (I) may acts as a light stabilizer.

The term "photostability" refers to the ability of a UV filter or any other molecule, which is exposed to sunlight, to stay stable upon irradiation. In particular, this means that the compound does not undergo a degradation process upon UV radiation.

The term "critical wavelength" is defined as the wavelength at which the area under the UV protection curve (% protection versus wavelength) represents 90% of the total area under the curve in the UV region (280-400 nm). For example, a critical wavelength of 370 nm indicates that the protection of the sunscreen composition is not limited to the wavelengths of UV-B, i.e. wavelengths from 280-320 nm, but extends to 370 nm in such a way that 90% of the total area under the protective curve in the UV region are reached at 370 nm.

The term "ultraviolet filter" or "UV filter" as used herein refers to organic or inorganic compounds, which can absorb and/or reflect UV radiation caused by sunlight. UV filter can be classified based on their UV protection curve as UV-A, UV-B or broadband filters. In the context of the present application, broadband filters may be listed as UV-A filters, as they also provide UV-A protection. In other words, preferred UV-A filters also include broadband filters.

The definition of "broadband" protection (also referred to as broad-spectrum or broad protection) is based on the "critical wavelength". For broadband coverage, UV-B and UV-A protection must be provided. According to the US requirements, a critical wavelength of at least 370 nm is required for achieving broad spectrum protection. Furthermore, it is recommended by the European Commission that all sunscreen or cosmetic compositions should have an UVA protection factor, which is at least one third of the labelled sun protection factor (SPF), e.g. if the sunscreen composition has an SPF of 30 the UVA protection factor has to be at least 10.

Preferred embodiments regarding the process according to the present invention are described hereinafter. It is to be understood that the preferred embodiments of the invention are preferred alone or in combination with each other.

As indicated above, the present invention relates in one embodiment to a process for isolating crystalline 2-(4'-diethylamino-2'-hydroxybenzoyl)benzoic acid hexyl ester comprising the steps of a) dissolving a mixture comprising 2-(4'-diethylamino-2'-hydroxybenzoyl)benzoic acid hexyl ester in a solvent having a boiling point of at most 110° C. to obtain a solution;

b) cooling the solution to a temperature in the range of from 20 to 40° C.;

c) optionally adding seed crystals of 2-(4'-diethylamino-2'-hydroxybenzoyl)benzoic acid hexyl ester to the solution;

d) cooling the solution to a temperature below 5° C. to obtain a suspension;

e) filtering the suspension to isolate 2-(4'-diethylamino-2'-hydroxybenzoyl)benzoic acid hexyl ester in crystalline form.

Preferred embodiments regarding the process are defined hereinafter.

In a preferred embodiment of the present invention, the mixture that is applied in step a) is pretreated in vacuo. Preferably, the mixture applied in step a) undergoes a pretreatment of drying the mixture in vacuo at a temperature of from 70 to 150° C., more preferably from 90 to 140° C., and in particular from 100 to 130° C., before dissolving in a solvent having a boiling point of at most 110° C. Preferably, the pretreatment is performed at a pressure from 0.1 to 800 mbar, more preferably 1 to 700 mbar, and in particular from 5 to 600 mbar. Preferably, the pretreatment is carried out 5 to 360 minutes, more preferably 10 to 250 minutes, and in particular 20 to 120 minutes.

In one embodiment of the present invention, the mixture in step a) comprises at least 85%, preferably at least 90%, by weight 2-(4'-diethylamino-2'-hydroxybenzoyl)benzoic acid hexyl ester and up to 15%, preferably up to 10%, impurities including solvent residues of solvents having a boiling point of more than 110° C. and phthalic acid dialkyl esters, wherein the weight-% amounts are in each case based on the total weight of the mixture.

In one embodiment of the present invention, the impurities include the solvents having a boiling point of more than 110° C. in an amount of up to 14%, preferably up to 12%, more preferably up to 10%, even more preferably up to 9%, and in particular up to 8%, by weight based on the total weight of the mixture and phthalic acid dialkyl esters in an amount of from 50 to 200 ppm, preferably from 55 to 150 ppm.

In this connection, it is to be understood that according to the present invention, phthalic acid dialkyl esters are defined by having the formula (A)

(A)

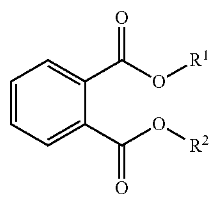

wherein $R^1$ and $R^2$ are $C_4$-$C_{12}$-alkyl, preferably wherein $R^1$ and $R^2$ are both n-hexyl.

In a preferred embodiment of the present invention, the impurities include 1-hexanol. In yet another preferred embodiment of the present invention, the impurities include 1-hexanol in an amount of up to 14%, preferably up to 12%, more preferably up to 10%, even more preferably up to 9%, and in particular up to 8%, by weight based on the total weight of the mixture and phthalic acid dihexyl esters in an amount of from 50 to 200 ppm, preferably from 55 to 150 ppm.

Toluene may also be an impurity according to the present invention, which may be comprised in the mixture applied in step a) in an amount of up to 10%, preferably up to 5% and in particular up to 3%, by weight based on the total weight of the mixture.

Further, according to the present invention, it is to be understood that impurities also comprise colored impurities. Especially, Rhodamine B (depicted by the formula (B)) and Rhodamine B derivatives. The C6-alkyl ester Rhodamine B derivative (depicted by the formula (C)) may be named as an exemplarily Rhodamine B derivative.

(B)

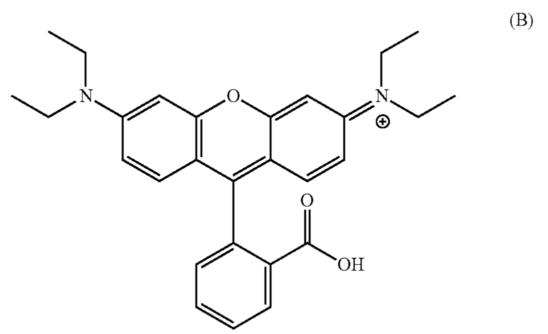

(C)

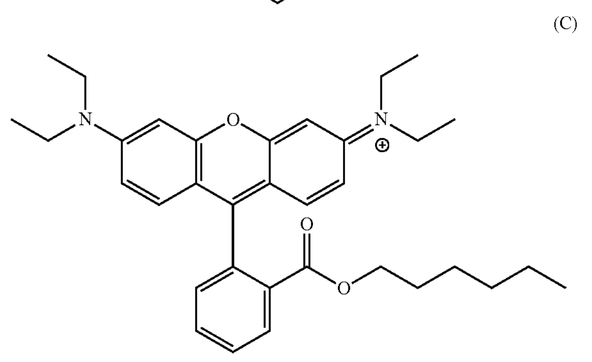

In one embodiment of the present invention, the mixture in step a) has a Gardner Value of more than 9.

In one embodiment of the present invention, the solvent in step a) has a boiling point of at most 100° C., preferably at most 90° C., more preferably at most 85° C., even more preferably at most 83° C., and in particular at most 80° C. In one embodiment of the present invention, the solvent in step a) has a boiling point in the range of from 30 to 110° C., preferably from 40 to 100° C., more preferably from 45 to 90° C., even more preferably from 50 to 85° C., and in particular from 60 to 85° C.

In one embodiment of the present invention, the solvent in step a) is polar. It is to be understood that a polar solvent has a dielectric constant (ε) of 15 or more, preferably of 18 or more. In a preferred embodiment of the present invention, the solvent in step a) has a dielectric constant (ε) of from 15 to 100. The polarity may alternatively or additionally be expressed by a dipole moment (μ) of from more than 1, preferably more than 2. In one embodiment of the present invention, the solvent in step a) has a dipole moment (μ) of from 1 to 10, preferably from more than 2 to 10, more preferably from 3 to 8. The dipole moment (μ) is indicated as Debye. In a preferred embodiment of the present invention, the solvent in step a) has a dielectric constant (ε) of from 15 to 100 and a dipole moment (μ) of from 1 to 10.

In one embodiment of the present invention, the solvent in step a) has low toxicity and is preferentially miscible with water. Solvents with low toxicity are e.g. described in the international council for harmonisation of technical requirements for pharmaceuticals for human use, ICH harmonised guideline, impurities: guideline for residual solvents, Q3C (R6) and toxicological data for class 3 solvents, Q3C support document 3. Acetone, isopropyl acetate, methyl acetate, 2-butanol, methylethyl ketone, tert-butyl methyl ether, ethanol, ethyl acetate, 1-propanol, ethyl ether, 2-propanol, ethyl formate, propyl acetate, formic acid, and trimethylamine may be named as suitable solvents.

In one embodiment of the present invention, the solvent in step a) is an alcohol, preferably is selected from methanol, ethanol, 2-methyl-2-propanol, 1-propanol, and isopropanol, which may be further substituted with a halogen (such as to obtain 2,2,2-trifluoromethanol, 2,2,2-trifluoroethanol, or 2-fluoroethanol). In a particular embodiment of the present invention, the solvent in step a) is selected from methanol, ethanol, 1-propanol, and isopropanol, preferably is ethanol. It is to be understood that according to the present invention, the solvent in step a) may be a mixture of the above solvents.

In one embodiment of the present invention, the mixture in step a) is dissolved at a temperature of at least 30° C., preferably of at least 35° C., more preferably of at least 40° C., and even more preferably of at least 45° C. In a preferred embodiment of the present invention, in step a) the mixture is dissolved at a temperature of from 35 to 80° C., preferably from 40 to 60° C., more preferably from 45 to 55° C., and in particular from 48 to 52° C.

In one embodiment of the present invention, the mixture and the solvent having a boiling point of at most 110° C. in step a) have a ratio of from 1:1.5 to 1:3.5, preferably from 1:1.7 to 1:3.1, more preferably from 1:1.8 to 1:3, and in particular from 1:1.9 to 1:2.9.

In one embodiment of the present invention, the solvent in step a) is not a non-polar solvent. It is to be understood that a non-polar solvent has a dielectric constant (ε) of less than 15. The non-polarity may alternatively or additionally be expressed by a dipole moment (μ) of from 0 to 0.5.

In one embodiment of the present invention, the solvent in step a) is not selected from the group consisting of petroleum ether, ligroin, n-hexane, cyclohexane, heptane, di-n-butyl ether, xylene, toluene, and benzene. In yet another embodiment of the present invention, the process does not comprise the addition of a solvent selected from the group consisting of petroleum ether, ligroin, n-hexane, cyclohexane, heptane, di-n-butyl ether, xylene, toluene, and benzene.

In step b) the solution is cooled to a temperature in the range of from 20 to 40° C., preferably from 20 to 35° C., more preferably from 20 to 30° C.

In one embodiment of the present invention, in step b) the solution is cooled to a temperature of from 20° C. to 40° C., preferably from 22 to 35° C., more preferably from 25 to 30° C., over a period of at least 10 minutes, preferably at least 15 minutes, more preferably at least 20 minutes, and in particular at least 25 minutes. In a preferred embodiment of the present invention, in step b) the solution is cooled to a temperature of from 20° C. to 30° C., preferably from 22° C. to 28° C., over a period of at least 10 minutes, preferably at least 15 minutes, more preferably at least 20 minutes, and in particular at least 25 minutes.

In one embodiment of the present invention, in step b) the solution is cooled to a temperature of from 20° C. to 40° C., preferably from 22 to 35° C., more preferably from 25 to 30° C., at a cooling rate of from 10 to 100° C./hour, preferably from 15 to 90° C./hour, more preferably from to 70° C./hour, and in particular from 25 to 60° C./hour. In a preferred embodiment of the present invention, in step b) the solution is cooled to a temperature of from 20° C. to 30° C., preferably from 22° C. to 28° C., at a cooling rate of from 10 to 100° C./hour, preferably from 15 to 90° C./hour, more preferably from 20 to 70° C./hour, and in particular from 25 to 60° C./hour.

In one embodiment of the present invention, cooling in step b) is performed via a linear or non-linear cooling rate.

In one embodiment of the present invention, in step c) crystals of 2-(4'-diethylamino-2'-hydroxybenzoyl)benzoic acid hexyl ester are added to the solution.

In one embodiment of the present invention, the seed crystals containing solution in step c) is stirred at a temperature of from more than 20° C. to less than 40° C., preferably from 22 to 35° C., and more preferably from 25 to 30° C., for a period of from 1 to 60 minutes, preferably from 1 to 50 minutes, more preferably from 2 to 40 minutes, and in particular from 3 to 25 minutes.

In one embodiment of the present invention, in step d) the solution is cooled to a temperature below 5° C., preferably below 0° C., more preferably below −3° C., even more preferably below −5° C., and in particular below −7° C., over a period of at least 2 hours, preferably at least 3 hours, more preferably at least 4 hours, and in particular at least 5 hours.

In one embodiment of the present invention, in step d) the solution is cooled to a temperature below 5° C., preferably below 0° C., more preferably below −3° C., even more preferably below −5° C., and in particular below −7° C., at a cooling rate of from more than 4 to less than 20° C./hour, preferably from 4.5 to 15° C./hours, more preferably from 5 to 11° C./hours, and in particular from 5 to 10° C./hours.

In one embodiment of the present invention, cooling in step d) is performed via a linear or non-linear cooling rate.

In one embodiment of the present invention, step d) further comprises stirring the obtained suspension at a temperature below 5° C., preferably below 0° C., more preferably below −3° C., even more preferably below −5° C., and in particular below −7° C., for at least 3 hours, preferably at least 4 hours, more preferably at least 5 hours, and in particular at least 6 hours.

In one embodiment of the present invention, step e) is performed at a temperature below 5° C., preferably below 0° C., more preferably below −3° C., even more preferably below −5° C., and in particular below −7° C.

In one embodiment of the present invention, subsequent to step e), the isolated 2-(4'-diethylamino-2'-hydroxybenzoyl)benzoic acid hexyl ester in crystalline form is suspended at least once more in a solvent at a temperature below 5° C., preferably below 0° C., more preferably below −3° C., even more preferably below −5° C., and in particular below −7° C. In one embodiment of the present invention, the at least one additional suspending step is performed at the same temperature as in step e). In this connection, the solvent used is a solvent having a boiling point of at most 110° C., wherein the solvent is preferable the same solvent as previously used in step a), more preferably, wherein the solvent is selected from methanol, ethanol, 1-propanol, and isopropanol, and in particular is ethanol. Subsequent to the at least one additional suspending step, the isolated 2-(4'-diethylamino-2'-hydroxybenzoyl)benzoic acid hexyl ester in crystalline form is filtered at a temperature below 5° C., preferably below 0° C., more preferably below −3° C., even more preferably below −5° C., and in particular below −7° C.

In one embodiment of the present invention, the process further comprises the step of f) washing the isolated 2-(4'-diethylamino-2'-hydroxybenzoyl)benzoic acid hexyl ester with a solvent, optionally an aqueous base, optionally a surfactant, and optionally water.

It is to be understood that the washing step f) may be performed with any suitable known solvent as above-outlined in more detail. Preferably, the solvent in step f) is the solvent as used in step a) of the process.

In one embodiment of the present invention, the aqueous base is present in step f) and is a potassium or sodium carbonate solution, a potassium or sodium hydrogen carbonate solution, a potassium or sodium hydroxide solution, or an aqueous ammonia solution. In a particular embodiment of the present invention, the aqueous base is present in step f) and is a sodium carbonate solution.

In one embodiment of the present invention, step f) further comprises washing with an acid solution. In this connection, inorganic acids such as aqueous hydrogen chloride solution and organic acids such as aqueous citric acid solution may be named.

In one embodiment of the present invention, the surfactant is present in step f) and is selected from the group consisting of anionic surfactant, cationic surfactant, amphoteric surfactant, and nonionic surfactant.

Preferred are surfactants, which are used in cosmetic formulations, which are derived from natural products, and/or which are biodegradable.

In one embodiment of the present invention, the surfactant is present in step f) and is selected from the group consisting of alkylbenzylsulfonate, sodium lauryl sulfate, ammonium laureth sulfate, disodium lauryl sulfosuccinate, cocoamphocarboxy-glycinate, decyl polyglucoside, cetearyl alcohol, stearyl alcohol, cocamidopropyl betaine, decyl glucoside, glyceryl cocoate, sodium cocoyl Isethionate, almond glycerides, sodium lauryl sulpho-acetate, sodium lauroyl sarcosinate, sodium methyl cocoyl taurate, sucrose cocoate, polysorbate 20, and polysorbate 80, preferably dodecylbenzene sulfonic acid sodium salt.

In one embodiment of the present invention, step f) is performed at a temperature of at least −5° C., preferably at least −2° C., more preferably at least 0° C., and in particular at least 3° C.

In one embodiment of the present invention, the process further comprises the step of g) drying the isolated 2-(4'-diethylamino-2'-hydroxybenzoyl)benzoic acid hexyl ester. It is to be understood that every appropriate drying method may be applied.

In one embodiment of the present invention, the drying step g) is performed in vacuo at a temperature of less than 55° C., preferably of less than 50° C. In one embodiment of the present invention, the drying step g) is performed in vacuo at a temperature from 25 to 55° C., preferably from 25 to 50° C., and in particular from 30 to 45° C.

In one embodiment of the present invention, the process does not comprise the addition of activated carbon.

In one embodiment of the present invention, the process does not comprise adsorption over a silicic acid bed.

In a particular embodiment of the present invention, the process does not comprise adsorption over an activated carbon or silicic acid bed.

After drying, a free flowing crystalline solid of 2-(4'-Diethylamino-2'-hydroxybenzoyl)benzoic acid hexyl ester is obtained.

In one embodiment of the present invention, the process provides crystalline 2-(4'-diethylamino-2'-hydroxybenzoyl) benzoic acid hexyl ester having a phthalic acid dialkyl ester content of less than 40 ppm, preferably of less than 30 ppm, more preferably of less than 15 ppm, even more preferably of less than 10 ppm, and in particular of less than 5 ppm. In one particular preferred embodiment of the present invention, the process provides crystalline 2-(4'-diethylamino-2'-hydroxybenzoyl)benzoic acid hexyl ester having a phthalic acid dialkyl ester content of less than 4 ppm, preferably of less than 3 ppm, more preferably of less than 2 ppm, and in particular of less than 1 ppm.

In this connection, it is to be understood that the present invention provides a process for isolating crystalline 2-(4'-diethylamino-2'-hydroxybenzoyl)benzoic acid hexyl ester having a reduced phthalic acid dihexyl ester (also known as dihexyl phthalate) content, preferably with a phthalic acid dihexyl ester content of less than 15 ppm, more preferably of less than 10 ppm, even more preferably of less than 5 ppm, still more preferably less than 2 ppm, and in particular of less than 1 ppm.

In one embodiment of the present invention, the process provides crystalline 2-(4'-diethylamino-2'-hydroxybenzoyl) benzoic acid hexyl ester having colored impurities content of less than 5 ppm, preferably of less than 3 ppm, and in particular of less than 1 ppm.

In this connection, the present invention provides a process for isolating crystalline 2-(4'-diethylamino-2'-hydroxybenzoyl)benzoic acid hexyl ester having a reduced Rhodamine B content, preferably with a Rhodamine B content of less than 5 ppm, more preferably of less than 3 ppm, and in particular of less than 1 ppm.

In one embodiment of the present invention, the process provides crystalline 2-(4'-diethylamino-2'-hydroxybenzoyl) benzoic acid hexyl ester having a Gardner value of 9 or lower, preferably of 8.8 or lower, more preferably of 8.6 or lower, even more preferably of 8.4 or lower, and in particular of 8.3 or lower.

In one embodiment of the present invention, the process provides crystalline 2-(4'-diethylamino-2'-hydroxybenzoyl) benzoic acid hexyl ester having a solvent content of less than 500 ppm, preferably of less than 400 ppm, more preferably of less than 300 ppm, even more preferably of less than 200 ppm, still more preferably of less than 100 ppm, and in particular of less than 50 ppm. In this connection, it is to be understood that the solvent content to which it is referred to includes the impurities derived from solvent residues of solvents having a boiling point of more than 110° C.

In one embodiment of the present invention, the process provides crystalline 2-(4'-diethylamino-2'-hydroxybenzoyl) benzoic acid hexyl ester having a 1-hexanol content of less than 400 ppm, preferably of less than 200 ppm, more preferably of less than 150 ppm, even more preferably of less than 100 ppm, still more preferably of less than 50 ppm, and in particular of less than 40 ppm.

In one preferred embodiment of the present invention, the process provides crystalline 2-(4'-diethylamino-2'-hydroxybenzoyl)benzoic acid hexyl ester having a toluene content of less than 300 ppm, preferably of less than 200 ppm, more preferably of less than 150 ppm, even more preferably of less than 100 ppm, still more preferably of less than 40 ppm, and in particular of less than 20 ppm.

In one embodiment of the present invention, the isolated 2-(4'-diethylamino-2'-hydroxybenzoyl)benzoic acid hexyl ester has a purity of at least 99%, preferably of at least 99.2%, more preferably of at least 99.4%, even more preferably of at least 99.6%, and in particular of more than 99.8%.

In one embodiment of the present invention, the isolated 2-(4'-diethylamino-2'-hydroxybenzoyl)benzoic acid hexyl ester has a purity of at least 99%, a phthalic acid dialkyl ester content of less than 15 ppm, a solvent content of less than 400 ppm, and a Gardner value of 8.3 or lower, and wherein preferably the isolated 2-(4'-diethylamino-2'-hydroxybenzoyl)benzoic acid hexyl ester has a purity of at least 99%, a phthalic acid dialkyl ester content of less than 5 ppm, a solvent content of less than 400 ppm, a Gardner value of 8.3 or lower, and a rhodamine B content of less than 1 ppm. Preferably the solvents are selected from the group consisting of 1-hexanole, toluene, and mixtures thereof.

In one embodiment of the present invention, the isolated 2-(4'-diethylamino-2'-hydroxybenzoyl)benzoic acid hexyl ester has a purity of at least 99%, a phthalic acid dialkyl ester content of less than 1 ppm, a solvent content of less than 400 ppm, a Gardner value of 8.3 or lower, and a rhodamine B content of less than 1 ppm.

In one embodiment of the present invention, the isolated 2-(4'-diethylamino-2'-hydroxybenzoyl)benzoic acid hexyl ester has a purity of at least 99%, a phthalic acid dialkyl ester content of less than 3 ppm, a toluene content of less than 300 ppm, a 1-hexanol content of less than 400 ppm, a rhodamine B content of less than 1 ppm, and/or a Gardner value of 8.3 or lower.

In one embodiment of the present invention, the isolated 2-(4'-diethylamino-2'-hydroxybenzoyl)benzoic acid hexyl ester has a purity of at least 99%, a phthalic acid dialkyl ester content of less than 5 ppm, a solvent content of less than 100 ppm, and a Gardner value of 8.3 or lower. Preferably the solvents are selected from the group consisting of 1-hexanole, toluene, and mixtures thereof.

In one embodiment of the present invention, the isolated 2-(4'-diethylamino-2'-hydroxybenzoyl)benzoic acid hexyl ester has a purity of at least 99%, a phthalic acid dihexyl ester content of less than 15 ppm, a 1-hexanol content of less than 400 ppm, and a Gardner value of 8.3 or lower, and wherein preferably the isolated 2-(4'-diethylamino-2'-hydroxybenzoyl)benzoic acid hexyl ester has a purity of at least 99%, a phthalic acid dihexyl ester content of less than 5 ppm, a 1-hexanol content of less than 200 ppm, a Gardner value of 8.3 or lower, and a rhodamine B content of less than 1 ppm.

In one embodiment of the present invention, the isolated 2-(4'-diethylamino-2'-hydroxybenzoyl)benzoic acid hexyl ester has a purity of at least 99%, a phthalic acid dihexyl ester content of less than 5 ppm, a 1-hexanol content of less than 400 ppm, a toluene content of less than 300 ppm, and a Gardner value of 8.3 or lower.

In one embodiment of the present invention, the isolated 2-(4'-diethylamino-2'-hydroxybenzoyl)benzoic acid hexyl ester has a purity of at least 99%, a phthalic acid dialkyl ester content of less than 15 ppm, a solvent content of less than 200 ppm, and a Gardner value of 8.3 or lower, and wherein preferably the isolated 2-(4'-diethylamino-2'-hydroxybenzoyl)benzoic acid hexyl ester has a purity of at least 99%, a phthalic acid dialkyl ester content of less than 5 ppm, a solvent content of less than 200 ppm, a Gardner value of 8.3 or lower, and a rhodamine B content of less than 1 ppm.

In one embodiment of the present invention, the isolated 2-(4'-diethylamino-2'-hydroxybenzoyl)benzoic acid hexyl ester has a purity of at least 99%, a phthalic acid dialkyl ester content of less than 1 ppm, a solvent content of less than 200 ppm, a Gardner value of 8.3 or lower, and a rhodamine B content of less than 1 ppm.

In one embodiment of the present invention, the isolated 2-(4'-diethylamino-2'-hydroxybenzoyl)benzoic acid hexyl ester has a purity of at least 99%, a phthalic acid dialkyl ester content of less than 3 ppm, a toluene content of less than 1 ppm, a 1-hexanol content of less than 200 ppm, a rhodamine B content of less than 1 ppm, and a Gardner value of 8.3 or lower.

In one embodiment of the present invention, the isolated 2-(4'-diethylamino-2'-hydroxybenzoyl)benzoic acid hexyl ester has a purity of at least 99%, a phthalic acid dialkyl ester content of less than 1 ppm, a solvent content of less than 200 ppm, and a Gardner value of 8.3 or lower.

In one embodiment of the present invention, the isolated 2-(4'-diethylamino-2'-hydroxybenzoyl)benzoic acid hexyl ester has a purity of at least 99%, a phthalic acid dihexyl ester content of less than 15 ppm, a solvent content of less than 200 ppm, and a Gardner value of 8.3 or lower, and wherein preferably the isolated 2-(4'-diethylamino-2'-hydroxybenzoyl)benzoic acid hexyl ester has a purity of at least 99%, a phthalic acid dihexyl ester content of less than 5 ppm, a solvent content of less than 200 ppm, a Gardner value of 8.3 or lower, and a rhodamine B content of less than 1 ppm.

In one embodiment of the present invention, the isolated 2-(4'-diethylamino-2'-hydroxybenzoyl)benzoic acid hexyl ester has a purity of at least 99%, a phthalic acid dihexyl ester content of less than 1 ppm, a solvent content of less than 200 ppm, a Gardner value of 8.3 or lower, and a rhodamine B content of less than 1 ppm.

In one embodiment, the present invention relates to crystals of 2-(4'-diethylamino-2'-hydroxybenzoyl)benzoic acid hexyl ester obtained according to the claimed process. Preferably the obtained crystals have a purity of at least 99%, a phthalic acid dialkyl ester content of less than 15 ppm, a solvent content of less than 200 ppm, and a Gardner value of 8.3 or lower, more preferably a purity of at least 99%, a phthalic acid dihexyl ester content of less than 5 ppm, a solvent content of less than 200 ppm, a Gardner value of 8.3 or lower, and a rhodamine content of less than 1 ppm. In another preferred embodiment the obtained crystals have a purity of at least 99%, a phthalic acid dialkyl ester content of less than 15 ppm, a 1-hexanol content of less than 400 ppm, and a Gardner value of 8.3 or lower, more preferably a purity of at least 99%, a phthalic acid dihexyl ester content of less than 5 ppm, a 1-hexanol content of less than 200 ppm, a Gardner value of 8.3 or lower, and a rhodamine content of less than 1 ppm.

The process according to the present invention provides 2-(4'-diethylamino-2'-hydroxybenzoyl)benzoic acid hexyl ester having a particularly low content of impurities. Surprisingly, the process according to the present invention provides 2-(4'-diethylamino-2'-hydroxybenzoyl)benzoic acid hexyl ester having a particularly low phthalic acid dialkyl ester content. According to the present invention, the determination of phthalate esters and rhodamine type impurities is preferably performed by HPLC analysis. Preferably, the determination of the solvent residues is performed by GC analysis.

In one embodiment, the present invention relates to 2-(4'-diethylamino-2'-hydroxybenzoyl)benzoic acid hexyl ester having a phthalic acid dialkyl ester content of less than ppm, preferably of less than 10 ppm, more preferably of less than 5 ppm, even more preferably less than 2 ppm, and in particular of less than 1 ppm.

In a particular embodiment, the present invention relates to 2-(4'-diethylamino-2'-hydroxybenzoyl)benzoic acid hexyl ester having a phthalic acid dihexyl ester content of less than 15 ppm, preferably of less than 10 ppm, more preferably of less than 5 ppm, even more preferably less than 2 ppm, and in particular of less than 1 ppm.

In one embodiment, the present invention relates to 2-(4'-diethylamino-2'-hydroxybenzoyl)benzoic acid hexyl ester having a purity of at least 99%, a phthalic acid dialkyl ester content of less than 15 ppm, a 1-hexanol content of less than 400 ppm, and a Gardner value of 8.3 or lower, and wherein preferably the 2-(4'-diethylamino-2'-hydroxybenzoyl)benzoic acid hexyl ester has a purity of at least 99%, a phthalic acid dihexyl ester content of less than 5 ppm, a 1-hexanol content of less than 200 ppm, a Gardner value of 8.3 or lower, and a rhodamine content of less than 1 ppm.

In a preferred embodiment, the present invention relates to 2-(4'-diethylamino-2'-hydroxybenzoyl)benzoic acid hexyl ester having a purity of at least 99%, a phthalic acid dialkyl ester content of less than 15 ppm, a 1-hexanol content of less than 400 ppm, a toluene content of less than 300 ppm, and a Gardner value of 8.3 or lower, and wherein preferably the 2-(4'-diethylamino-2'-hydroxybenzoyl)benzoic acid hexyl ester has a purity of at least 99%, a phthalic acid dihexyl ester content of less than 5 ppm, a 1-hexanol content of less than 200 ppm, a toluene content of less than 100 ppm, and a Gardner value of 8.3 or lower.

In one embodiment, the present invention relates to 2-(4'-diethylamino-2'-hydroxybenzoyl)benzoic acid hexyl ester having a purity of at least 99%, a phthalic acid dialkyl ester content of less than 15 ppm, a solvent content of less than 200 ppm, and a Gardner value of 8.3 or lower, and wherein preferably the 2-(4'-diethylamino-2'-hydroxybenzoyl)benzoic acid hexyl ester has a purity of at least 99%, a phthalic acid dihexyl ester content of less than 5 ppm, a solvent content of less than 200 ppm, a Gardner value of 8.3 or lower, and a rhodamine content of less than 1 ppm.

In one embodiment, the present invention relates to a body-care product or a daily care composition comprising the crystals of 2-(4'-diethylamino-2'-hydroxybenzoyl)benzoic acid hexyl ester obtained according to the claimed process. In particular, the present invention relates to a sunscreen composition comprising the crystals of 2-(4'-diethylamino-2'-hydroxybenzoyl)benzoic acid hexyl ester obtained according to the claimed process.

In one embodiment, the present invention relates to the use of the crystals of 2-(4'-diethylamino-2'-hydroxybenzoyl) benzoic acid hexyl ester obtained according to the claimed process as UV filter in a body-care product or a daily care composition, in particular in a sunscreen composition.

The present invention is further illustrated by the following examples.

EXAMPLES

Methods

The determination of 2-(4'-diethylamino-2'-hydroxybenzoyl)benzoic acid hexyl ester and solvent residues was performed using GC analysis.

Agilent 6890 Plus GC with FID (flame ionization detector). Fused silica capillary column (100% dimethylpolysiloxane film (0.33 μm), e.g. Agilent 19091-60321, 12 m×0.2 mm. Helium, constant flow, split 150:1, injector temperature 250° C., detector temperature 320° C., injection volume 1 μL. Gradient: 2 min T=80° C., 10° C./min (80-320° C.), 4 min T=320° C.

External standards: Toluene, n-hexanol, 2-(4'-diethylamino-2'-hydroxybenzoyl)benzoic acid hexyl ester, ethanol, 2-propanol.

The determination of phthalate esters and rhodamine type impurities was performed using H PLC analysis.

Agilent 1290 HPLC with diode array detector (190-640 nm). Zorbax Eclipse XDB C8 3×100 mm, 1.8 μm (Agilent Nr. 993967-906) HPLC column.

Solvent A: Water/acetonitrile 9:1+TBAHS (tetrabutylammonium hydrogen sulfate) 2 g/L.

Solvent B: Acetonitrile (0.8 mL/min). Injection volume 5 μL, T=50° C. Gradient: t=0 min 100% A, 0% B/t=21 min, 0% A, 100% B/t=23 min, 0% A, 100% B/t=24 min, 100% A, 0% B (post time 4 min).

Rhodamine B: RT=8.2 min (558 nm), Di-n-hexylphthalate: RT (retention time)=17.3 min (200 nm, subtraction of 356 nm signals). External standards: Rhodamine B, Di-n-hexylphthalate.

The Gardner value has been determined by spectral color measurement of clear molten 2-(4'-Diethylamino-2'-hydroxybenzoyl)benzoic acid hexyl ester (Lico 500 colorimeter, Hach Lange GmbH, Germany).

Analytical standards for calibration have been performed by standard state of the art methods.

Example 1

Hexanol-moist, pink-colored crude 2-(4'-Diethylamino-2'-hydroxybenzoyl)benzoic acid hexyl ester is prepared according to US2005/0165099, example 2. The crude product is dried with suction.

Composition of the crude product: 93% 2-(4'-Diethylamino-2'-hydroxybenzoyl)benzoic acid hexyl ester, 7% solvent residues and impurities (81 ppm PSDHE, Gardner Value >9)

The crude 2-(4'-Diethylamino-2'-hydroxybenzoyl)benzoic acid hexyl ester (299.8 g) is dissolved in ethanol (836.4 g) at 50° C., then cooled down to 25° C. within 30-50 min (linear cooling ramp). Afterwards seed crystals of pure 2-(4'-Diethylamino-2'-hydroxybenzoyl)benzoic acid hexyl ester (0.012 g) are added and the mixture is stirred for 5-10 min at 25° C. After cooling to −10° C. (10 h, linear cooling ramp.) a crystal suspension is obtained and further stirred for 7 h at −10° C. The solids are separated by filtration at −10° C. The crystals are suspended in cold ethanol (167 g) and separated by vacuum filtration (−10° C.). Subsequently the temperature is raised to 5° C. and the crystalline solid is washed successively with aqueous $Na_2CO_3$ solution (668 g, 2% $Na_2CO_3$), aqueous citric acid solution (670 g, 1% citric acid) and water. The product is dried in vacuo (45° C.) to give pure 2-(4'-Diethylamino-2'-hydroxybenzoyl)benzoic acid hexyl ester (258.1 g) as a near white free flowing crystalline solid.

Composition of the pure product: 99.9% 2-(4'-Diethylamino-2'-hydroxybenzoyl)benzoic acid hexyl ester, 190 ppm 1-Hexanol, 250 ppm Toluene, 6 ppm PSDHE, Gardner Value 8.1

Example 2

Hexanol-moist, pink-colored crude 2-(4'-Diethylamino-2'-hydroxybenzoyl)benzoic acid hexyl ester is prepared according to US2005/0165099, example 2. The crude product is dried with suction.

Composition of the crude product: 92% 2-(4'-Diethylamino-2'-hydroxybenzoyl)benzoic acid hexyl ester, 8% solvent residues and impurities (81 ppm PSDHE, Gardner Value >9)

The crude 2-(4'-Diethylamino-2'-hydroxybenzoyl)benzoic acid hexyl ester (302.7 g) is dissolved in ethanol (630.1 g) at 50° C., then cooled down to 25° C. within 30-50 min (linear cooling ramp). Afterwards seed crystals of pure 2-(4'-Diethylamino-2'-hydroxybenzoyl)benzoic acid hexyl ester (0.012 g) are added and the mixture is stirred for 5-10 min at 25° C. After cooling to −10° C. (10 h, linear cooling ramp.) a crystal suspension is obtained and further stirred for 6 h at −10° C. The solids are separated by filtration at −10° C. The crystals are suspended in cold ethanol (130-190 g) and separated by vacuum filtration (−10° C., repeated four times). Subsequently the temperature is raised to 5° C. and the crystalline solid is washed successively with aqueous $Na_2CO_3$/dodecylbenzene sulfonic acid sodium salt solution (504 g, 2% $Na_2CO_3$, 0.007 g dodecylbenzene sulfonic acid sodium salt), aqueous citric acid solution (504 g, 1% citric acid) and water. The product is dried in vacuo (45° C.) to give pure 2-(4'-Diethylamino-2'-hydroxybenzoyl)benzoic acid hexyl ester (262.7 g) as a near white free flowing crystalline solid.

Composition of the pure product: 99.9% 2-(4'-Diethylamino-2'-hydroxybenzoyl)benzoic acid hexyl ester, 310 ppm 1-Hexanol, 38 ppm Toluene, 2 ppm PSDHE, Gardner Value 8.3

Example 3

Hexanol-moist, pink-colored crude 2-(4'-Diethylamino-2'-hydroxybenzoyl)benzoic acid hexyl ester is prepared according to US2005/0165099, example 2. The crude product is dried in vacuo at 120° C. (rotary evaporator).

Composition of the crude product: 99.1% 2-(4'-Diethylamino-2'-hydroxybenzoyl)benzoic acid hexyl ester, 0.5% 1-Hexanol, 0.2% Toluene, 39.4 ppm Rhodamine B, 62 ppm PSDHE, Gardner Value 9

The crude 2-(4'-Diethylamino-2'-hydroxybenzoyl)benzoic acid hexyl ester (448.7 g) is dissolved in ethanol (547.9 g) at 37-50° C., then cooled down from 37 to 25° C. within 70 min (linear cooling ramp). Afterwards seed crystals of pure 2-(4'-Diethylamino-2'-hydroxybenzoyl)benzoic acid hexyl ester (9.0 g) are added and the mixture is stirred for 220 min at 25° C. After cooling to −10° C. (300 min, linear cooling ramp) a crystal suspension is obtained and further stirred for 6-8 h at −10° C. The solids are separated by filtration at −10° C. The crystals are suspended in cold ethanol (330 g) and separated by vacuum filtration (−10° C., repeated three times). The product is dried in vacuo (45° C.) to give pure 2-(4'-Diethylamino-2'-hydroxybenzoyl)benzoic acid hexyl ester (425.1 g) as a near white free flowing crystalline solid.

Composition of the pure product: 99.9% 2-(4'-Diethylamino-2'-hydroxybenzoyl)benzoic acid hexyl ester, <10 ppm 1-Hexanol, 10 ppm Toluene, 0.8 ppm PSDHE, 0.8 ppm Rhodamine B, Gardner Value 7.0

Example 4

Hexanol-moist, pink-colored crude 2-(4'-Diethylamino-2'-hydroxybenzoyl)benzoic acid hexyl ester is prepared according to US2005/0165099, example 2. The crude product is dried in vacuo at 120° C. (rotary evaporator).

Composition of the crude product: 99.1% 2-(4'-Diethylamino-2'-hydroxybenzoyl)benzoic acid hexyl ester, 0.5% 1-Hexanol, 0.2% Toluene, 39.4 ppm Rhodamine B, 62 ppm PSDHE, Gardner Value 9

The crude 2-(4'-Diethylamino-2'-hydroxybenzoyl)benzoic acid hexyl ester (449.0 g) is dissolved in ethanol (548.0 g) at 37-50° C., then cooled down from 37 to 25° C. within 70 min (linear cooling ramp). Afterwards seed crystals of pure 2-(4'-Diethylamino-2'-hydroxybenzoyl)benzoic acid hexyl ester (9.1 g) are added and the mixture is stirred for 220 min at 25° C. After cooling to −10° C. (300 min, linear cooling ramp) a crystal suspension is obtained and further stirred for 6-8 h at −10° C. The solids are separated by filtration at −10° C. The crystals are suspended in cold ethanol (452 g) and separated by vacuum filtration (−10° C., repeated three times). The product is dried in vacuo (45° C.) to give pure 2-(4'-Diethylamino-2'-hydroxybenzoyl)benzoic acid hexyl ester (426.0 g) as a near white free flowing crystalline solid.

Composition of the pure product: 99.7% 2-(4'-Diethylamino-2'-hydroxybenzoyl)benzoic acid hexyl ester, <10 ppm 1-Hexanol, 10 ppm Toluene, 0.8 ppm PSDHE, 0.8 ppm Rhodamine B, Gardner Value 7.0

Example 5

Hexanol-moist, pink-colored crude 2-(4'-Diethylamino-2'-hydroxybenzoyl)benzoic acid hexyl ester is prepared according to US2005/0165099, example 2. The crude product is dried in vacuo at 120° C. (rotary evaporator).

Composition of the crude product: 98.5% 2-(4'-Diethylamino-2'-hydroxybenzoyl)benzoic acid hexyl ester, 1.0% 1-Hexanol, 0.1% Toluene, 34.0 ppm Rhodamine B, 80 ppm PSDHE, Gardner Value 8.7

The crude 2-(4'-Diethylamino-2'-hydroxybenzoyl)benzoic acid hexyl ester (449.0 g) is dissolved in ethanol (550.1 g) at 37-50° C., then cooled down from 37 to 25° C. within 70 min (linear cooling ramp). Afterwards seed crystals of pure 2-(4'-Diethylamino-2'-hydroxybenzoyl)benzoic acid hexyl ester (9.0 g) are added and the mixture is stirred for 220 min at 25° C. After cooling to −10° C. (300 min, linear cooling ramp) a crystal suspension is obtained and further stirred for 6-8 h at −10° C. The solids are separated by filtration at −10° C. The crystals are suspended in cold ethanol (450 g) and separated by vacuum filtration (−10° C., repeated three times). Subsequently the temperature is raised to 5-10° C. and the crystalline solid is washed water (750 g). The product is dried in vacuo (45° C.) to give pure 2-(4'-Diethylamino-2'-hydroxybenzoyl)benzoic acid hexyl ester (428.1 g) as a near white free flowing crystalline solid.

Composition of the pure product: 99.8% 2-(4'-Diethylamino-2'-hydroxybenzoyl)benzoic acid hexyl ester, 30 ppm 1-Hexanol, 7 ppm Toluene, 0.9 ppm PSDHE, 0.6 ppm Rhodamine B, Gardner Value 7.1

Example 6

Hexanol-moist, pink-colored crude 2-(4'-Diethylamino-2'-hydroxybenzoyl)benzoic acid hexyl ester is prepared according to US2005/0165099, example 2. The crude product is dried in vacuo at 120° C. (rotary evaporator).

Composition of the crude product: 98.5% 2-(4'-Diethylamino-2'-hydroxybenzoyl)benzoic acid hexyl ester, 1.0% 1-Hexanol, 0.1% Toluene, 34.0 ppm Rhodamine B, 80 ppm PSDHE, Gardner Value 8.7

The crude 2-(4'-Diethylamino-2'-hydroxybenzoyl)benzoic acid hexyl ester (449.0 g) is dissolved in 2-propanol (550 g) at 37-50° C., then cooled down from 37 to 25° C. within 70 min (linear cooling ramp). Afterwards seed crystals of pure 2-(4'-Diethylamino-2'-hydroxybenzoyl)benzoic acid hexyl ester (9.1 g) are added and the mixture is stirred for 220 min at 25° C. After cooling to 0° C. (300 min, linear cooling ramp) a crystal suspension is obtained and further stirred for 6-8 h at 0° C. The solids are separated by filtration at 0° C. The crystals are suspended in cold 2-propanol (307-338 g) and separated by vacuum filtration (−0° C., repeated three times). Subsequently the temperature is raised to 5-15° C. and the crystalline solid is washed water (615 g). The product is dried in vacuo (45° C.) to give pure 2-(4'-Diethylamino-2'-hydroxybenzoyl)benzoic acid hexyl ester (432.4 g) as a near white free flowing crystalline solid.

Composition of the pure product: 99.8% 2-(4'-Diethylamino-2'-hydroxybenzoyl)benzoic acid hexyl ester 65 ppm 1-Hexanol, 15 ppm Toluene, 1.7 ppm PSDHE, 2.2 ppm Rhodamine B, Gardner Value 7.1

The invention claimed is:

1. A process for isolating crystalline 2-(4'-diethylamino-2'-hydroxybenzoyl)benzoic acid hexyl ester comprising the steps of a) dissolving a mixture comprising 2-(4'-diethylamino-2'-hydroxybenzoyl)benzoic acid hexyl ester in a solvent having a boiling point of at most 110° C. to obtain a solution;

b) cooling the solution to a temperature in the range of from 20 to 40° C.;

c) adding seed crystals of 2-(4'-diethylamino-2'-hydroxybenzoyl)benzoic acid hexyl ester to the solution;

d) cooling the solution to a temperature below 5° C. to obtain a suspension;

e) filtering the suspension to isolate 2-(4'-diethylamino-2'-hydroxybenzoyl)benzoic acid hexyl ester in crystalline form.

2. The process according to claim 1, wherein the mixture in step a) comprises at least 85% by weight 2-(4'-diethylamino-2'-hydroxybenzoyl)benzoic acid hexyl ester and up to 15% impurities including solvent residues of solvents having a boiling point of more than 110° C. and phthalic acid dialkyl esters, wherein the weight-% amounts are in each case based on the total weight of the mixture.

3. The process according to claim 1, wherein the solvent in step a) has a boiling point of at most 85° C.

4. The process according to claim 1, wherein the solvent in step a) is polar and/or is selected from methanol, ethanol, 1-propanol, and isopropanol.

5. The process according to claim 1, wherein in step a) the mixture is dissolved at a temperature of from 45 to 55° C.

6. The process according to claim 1, wherein in step b) the solution is cooled to a temperature of from 25 to 30° C. over a period of at least 10 minutes.

7. The process according to claim 1, wherein in step d) the solution is cooled to a temperature below −5° C. over a period of at least 3 hours.

8. The process according to claim 6, wherein cooling is performed via a linear or non-linear cooling rate.

9. The process according to claim 1, wherein step d) further comprises stirring the obtained suspension at a temperature below 0° C. for at least 3 hours.

10. The process according to claim 1, wherein the process further comprises the step of f) washing the isolated 2-(4'-diethylamino-2'-hydroxybenzoyl)benzoic acid hexyl ester with a solvent, optionally an aqueous base, optionally a surfactant, and optionally water.

11. The process according to claim 10, wherein the aqueous base is a potassium or sodium carbonate solution, a potassium or sodium hydrogen carbonate solution, a potassium or sodium hydroxide solution, or an aqueous ammonia solution.

12. The process according to claim 10, wherein the surfactant is selected from the group consisting of alkylbenzylsulfonate, sodium lauryl sulfate, ammonium laureth sulfate, disodium lauryl sulfosuccinate, cocoamphocarboxyglycinate, decyl polyglucoside, cetearyl alcohol, stearyl alcohol, cocamidopropyl betaine, decyl glucoside, glyceryl cocoate, sodium cocoyl Isethionate, almond glycerides, sodium lauryl sulphoacetate, sodium lauroyl sarcosinate, sodium methyl cocoyl taurate, sucrose cocoate, polysorbate 20, polysorbate 80, and mixtures thereof.

13. The process according to claim 10, wherein the process further comprises the step of g) drying the isolated 2-(4'-diethylamino-2'-hydroxybenzoyl)benzoic acid hexyl ester.

14. The process according to claim 1, wherein the isolated 2-(4'-diethylamino-2'-hydroxybenzoyl)benzoic acid hexyl ester has a purity of at least 99%, a phthalic acid dialkyl ester content of less than 15 ppm, a 1-hexanol content of less than 400 ppm, and a Gardner value of 8.3 or lower.

15. The process according to claim 1, wherein the isolated 2-(4'-diethylamino-2'-hydroxybenzoyl)benzoic acid hexyl ester has a purity of at least 99%, a phthalic acid dialkyl ester content of less than 1 ppm, a 1-hexanol content of less than 200 ppm, a Gardner value of 8.3 or lower, and a rhodamine content of less than 1 ppm.

* * * * *